(12) United States Patent
Carlsson et al.

(10) Patent No.: US 6,528,322 B1
(45) Date of Patent: Mar. 4, 2003

(54) ANALYTICAL METHOD AND APPARATUS

(75) Inventors: Jan Carlsson, Uppsala (SE); Maria Lönnberg, Knivsta (SE)

(73) Assignee: Pharmacia AB, Stockholm (SE)

( * ) Notice: Subject to any disclaimer, the term of this patent is extended or adjusted under 35 U.S.C. 154(b) by 153 days.

(21) Appl. No.: 09/633,110

(22) Filed: Aug. 4, 2000

Related U.S. Application Data

(60) Provisional application No. 60/148,566, filed on Aug. 13, 1999.

(30) Foreign Application Priority Data

Aug. 6, 1999 (SE) .................................................. 9902855

(51) Int. Cl.$^7$ ............................................. G01N 33/543
(52) U.S. Cl. ....................... 436/514; 436/518; 436/528; 436/530; 436/161; 436/102; 435/7.1; 435/287.9; 435/288.3; 204/400
(58) Field of Search ............................... 435/7.1, 287.9, 435/288.3; 436/518, 514, 528, 530, 161, 162; 204/400

(56) References Cited

U.S. PATENT DOCUMENTS

| | | |
|---|---|---|
| 4,313,906 A | 2/1982 | Filipi et al. |
| 4,469,601 A | 9/1984 | Beaver et al. |

FOREIGN PATENT DOCUMENTS

| | | |
|---|---|---|
| WO | WO9930145 | 6/1999 |

OTHER PUBLICATIONS

Pristoupil, T. I., Chromatog. Rev., vol. 12 (1970) pp. 109–125.

Primary Examiner—Bao-Thuy L. Nguyen
(74) Attorney, Agent, or Firm—Birch, Stewart, Kolasch & Birch, LLP

(57) ABSTRACT

The invention relates to a method for qualitative, semi-quantitative or quantitative determination of at least two analytes in an aqueous sample containing or suspected of containing the analytes, which method comprises the steps of:

(i) providing a flow matrix comprising a separation zone extending in a first dimension thereof, and a detection zone extending in the first dimension in a spaced parallel relationship with the separation zone, the detection zone comprising an immobilized reagent capable of capturing the analytes through biospecific interaction therewith, (ii) applying the sample to the flow matrix at or upstream of the separation zone, (iii) initiating a first essentially aqueous fluid flow in the flow matrix along the separation zone in the first dimension to transport the analytes through the separation zone to be separated therein, (iv) interrupting the first fluid flow and initiating a second essentially aqueous fluid flow in a second dimension of the flow matrix substantially transverse to the first dimension towards the detection zone to transport the separated analytes to the detection zone to be captured therein by the immobilized reagent, and (vi) determining the analytes in the detection zone. The invention also relates to an apparatus for carrying out the method.

33 Claims, 3 Drawing Sheets

ANALYTICAL METHOD AND APPARATUS

This application claims the benefit of No. 60/148,566, filed Aug. 13, 1999.

The present invention relates to a method and apparatus for determining analytes in a sample, and more particularly to a method and apparatus where the analytes are separated prior to detection.

BACKGROUND OF THE INVENTION

Biomolecules may be present in several heteroforms, such as isoforms, where small changes in the molecular structure may cause great changes in the effect of the molecule. Such small structural changes may, however, be difficult to measure specifically, even with methods of high specificity, such as immunoassays, as the compounds usually will compete for the binding to a specific antibody. In our copending international (PCT) application WO 99/60402, such structural changes are discussed and a method is disclosed for measuring some of the heteroforms, for example those having the highest positive or negative charge. The method in question uses a flow matrix having an application zone for sample and, downstream thereof, a detection zone with immobilized reagent which binds analyte and where bound analyte is detected. A separation zone is provided between the sample application zone and the detection zone. In the separation zone, disturbing components or components not to be determined are bound or retarded and prevented from reaching the detection zone with the analyte. If, for example, the analyte is one of two heteroforms, the other heteroform, which is not to be determined but would compete with the analyte for binding in the binding zone, is retarded in the separation zone to permit selective detection of the analyte. There may, however, often be more than two heteroforms. For example, transferrin may exist in at least nine different isoforms, where a few of the isoforms, primarily disialo transferrin but also asialo transferrin, are important to measure for testing alcohol abuse. To be able to measure all the isoforms in a complex mixture, it has so far been necessary to separate the isoforms by column chromatography, and then analyze each fraction for the presence of an isoform by spectrophotometric or immunoassay detection depending on the concentrations of the analytes to be measured.

WO 99/30145 discloses 2-dimensional gel electrophoresis for qualitative determination of nucleic acids, proteins, carbohydrates or lipids in a sample. The gel contains a separation gel with a sample loading zone and provided in a slot within the separation gel, a detection gel having an immobilized probe for one or more target molecules. After electrophoretic separation in the separation gel in a first dimension, the gel is rotated 90 degrees and electrophoresis is performed in a second dimension to transport the target molecule to the detection zone where binding of the target molecule to the immobilized probe is detected. There is no suggestion in WO 99/30145 that heteroforms could be determined. Also, electrophoretic systems are generally rather laborious and often expensive, especially when an additional detection step is to be included in the electrophoretic system.

U.S. Pat. No. 4,469,601 discloses a method and system for multi-dimensional chromatography in a thin-layer chromatographic plate wherein a sample is separated into an array of constituents. These constituents are then separated into a second array of sub-constituents by pumping a fluid through the plate in a direction crossing the array, and the sub-constituents are detected as they flow past fixed positions in this second direction. Thin layer chromatography is, however, restricted to the separation of small (i.e. low molecular weight) molecules, and does not permit the separation of biomolecules, such as proteins, for example.

Pristoupil, T. I., Chromatog. Rev., 12 (1970) 109–125 describes the use of nitrocellulose filters in chromatography and electrophoresis. Chromatography in aqueous solution was performed with a nitrocellulose membrane in a horizontal position in a plexiglass chamber. Proteins were detected by immersing the membrane in a staining solution, and other substances were detected by usual spray or sandwich techniques. On the intact membrane, proteins having a molecular weight of the order of $10^5$ and higher were firmly adsorbed on the membrane while peptides, amino acids and other low-molecular substances of hydrophilic character migrated with the front of the developing solution. For electrophoresis, it was necessary to impregnate the membrane with neutral detergents to prevent the high adsorption of proteins. Also immunochromatography of rabbit anti-bovine serum and immunochemically inactive normal rabbit serum on a membrane with bovine serum adsorbed thereto is described. The antigen-antibody complex gave a distinct spot at the start, while the immunochemically inactive proteins migrated without any marked adsorption. Thus, no "true" chromatography of components seems to have been obtained neither in the intact (or plain) membrane nor in the antibody-coated membrane but rather either firm binding or no binding at all.

There is therefore a need for an analytical method and apparatus which permit the determination of heteroforms of biomolecules and by which assays may be performed more quickly and more easily than by the prior art methods and apparatuses, respectively.

SUMMARY OF THE INVENTION

Accordingly, it is an object of the present invention to provide a determination method which overcomes the shortcomings of the prior art methods and which readily permits quick and reliable determination of all heteroforms of biomolecules, such as isoforms, even in a complex sample. It is a further object of the present invention to provide a determination method which may be performed on a single plate, sheet or chip. Still another object of the present invention is to provide a simple and easy-to-use apparatus of plate, sheet or chip type for performing the method of the present invention.

According to the present invention, the above and other objects and advantages are obtained by a method wherein analytes (such as isoforms) in an aqueous sample are separated in a flow matrix which permits capillary force assisted fluid flow therethrough, especially a planar flow matrix such as a chromatographic membrane (e.g. an ion exchange membrane). To determine the separated analytes, this being the gist of the invention, the separated analytes are eluted from the separation area of the flow matrix in a direction substantially transverse to the separation direction to migrate to a capture zone with immobilized reactant (such as a single immobilized antibody common to all the analytes), usually in the form of a line or band, where the eluted analytes are captured. There, the analytes may be detected and determined by the addition of a detection reagent capable of binding to the captured analytes. The detection reagent may e.g. be a suitably labelled antibody directed to the isoform, such as an antibody labelled by a black-coloured particle. In the latter case, for example, the varying colour intensity along the detection line or band may be readily detected and quantified by means of a scanner.

Essentially aqueous systems are used in the separation and elution steps. "Essentially aqueous" means here that the system is either completely aqueous or may contain a small amount, not more than about 3%, of one or more other solvents. Preferably, about 99%, more preferably about 99.5%, usually at least about 99.9% of the essentially aqueous system is water.

Thus, in one aspect the present invention provides a method for qualititative, semi-quantitative or quantitative determination of at least two analytes in an aqueous sample containing or suspected of containing said analytes, said method comprising the steps of:

(i) providing a flow matrix comprising a separation zone extending in a first dimension thereof, and a detection zone extending in said first dimension in a spaced parallel relationship with the separation zone, said detection zone comprising an immobilized reagent capable of capturing said analytes through biospecific interaction therewith, (ii) applying said sample to the flow matrix at or upstream of said separation zone, (iii) initiating a first essentially aqueous fluid flow in the flow matrix along the separation zone in said first dimension to transport said analytes through said separation zone to be separated therein, (iv) interrupting said first fluid flow and initiating a second essentially aqueous fluid flow in a second dimension of the flow matrix substantially transverse to said first dimension towards the detection zone, to transport said separated analytes to the detection zone to be captured therein by said immobilized reagent, and (v) determining said analytes in said detection zone.

In another aspect, the present invention provides an apparatus for carrying out the method of the invention, which apparatus comprises:

(i) a flow matrix having a separation zone and a detection zone extending in a spaced parallel relationship in a first dimension of the flow matrix, wherein the detection zone comprises immobilized reagent capable of binding the analytes through specific interaction therewith, (ii) means for initiating a first essentially aqueous fluid flow in the flow matrix along the separation zone in said first dimension of the flow matrix, (iii) means for initiating a second essentially aqueous fluid flow in a second dimension of said flow matrix substantially transverse to the said first dimension towards the detection zone, such that when a sample containing the analytes is introduced into to the separation zone, the analytes may be separated in the separation zone by said first fluid flow through the separation zone and transported by said second fluid flow to the detection zone where the analytes are bound to the immobilized reagent to be determined.

Preferably, the flow matrix is at least substantially planar.

The separation zone and the detection zone (which may be integral or two separate parts joined to each other) may either be arranged in the same plane of the flow matrix, or be arranged on top of each other. In the latter case, the two zones must be prevented from contacting each other such as by a removable partitioning element when the separation phase of the method of the invention is performed. Such a separating element may be a film or the like that is removed prior to performing steps (iv) and (v) above.

DETAILED DESCRIPTION OF THE INVENTION

Figure 1:
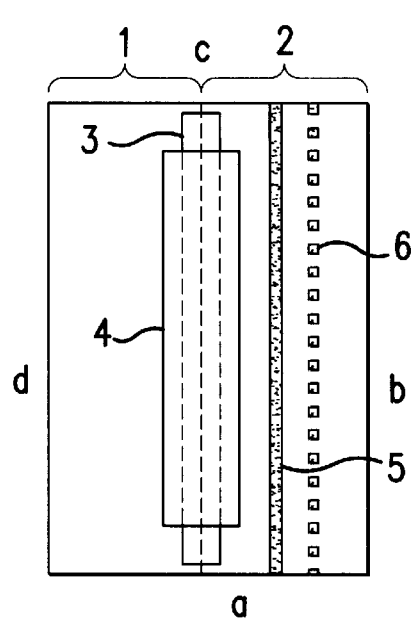
FIG. 1 is a schematic planar view of an embodiment of apparatus according to the present invention.

As mentioned above, the method of present invention is particularly useful for determining heteroforms of biomolecules, i.e. closely related biomolecular analytes, which may not be distinguished by a specific ligand or receptor, such as an antibody. Exemplary heteroforms include isoforms of proteins, e.g. differently glycosylated proteins (glycoproteins) where small variations in the carbohydrate structure can give isoforms with different isoelectric points, isoenzymes, etc. The term heteroforms also includes inter alia different forms of bioaffine complexes, where one part of the complex belongs to the isoform protein, e.g. free and antibody bound molecules. A so-called inhibition test may be used to determine if two compounds are heteroforms to one another. Reacting the ligand with one or both of the suspected isoforms and comparing the result, makes it possible to decide if the molecules are isoforms.

Glycoproteins such as transferrin, FSH, LH and TSH are examples of analytes that occur in a variety of isoforms, the relative occurrence of which is of clinical importance but which usually are not possible to differentiate by immunoassays as they are very similar from an immunochemical point of view. Other examples of present interest are so-called cardiac markers (e.g. creatine kinases) which occur in different isoforms with different charges as a result of protolytic degradation in the extracellular milieu.

Transferrin and their isoforms of interest are present in rather high concentrations in blood and can be analysed by spectrophotometric on-line detection (Jeppsson, J.-O., Clin. Chem. 39/10, 2115–2120 (1993)) directly after column separation, if enough amount of sample is applied on the column. Other molecules such as the hormones FSH, LH and TSH are present in low concentrations which require immunoasssay detection (Wide, L., Acta Endocronologica 1985, 109: 181–189).

In the method of the invention, the separation of analytes such as isoforms may be performed by applying the sample containing the isoforms on a planar flow matrix, especially a membrane, separating the isoforms by a first liquid flow in a separation area of the flow matrix, and then eluting the separated isoforms through a second liquid flow transverse to the first liquid flow such that the the isoforms are removed from the separation area and pass a detection area containing immobilized capturing reagent, usually as a line or band, to be captured thereby. The captured isoforms may then be detected by the application of a detecting reagent, e.g. a labelled antibody to the isoform which, for example, may be added via a third fluid flow in the same, opposite or transverse direction to that of the above-mentioned second flow.

In a (presently less preferred) embodiment, the separation zone and the detection zone may be provided on two separate flow matrix members placed on top of each other and separated by a removable film or the like which is removed prior to elution of the separated analytes and transport thereof to the detection zone.

A planar flow matrix, such as a membrane, designed for such an analysis comprises a separation zone, and in parallel and spaced thereto, a detection zone containing one or more lines or bands of immobilized capturing reagent extending along the detection zone.

As is readily seen from the above, and as will be better understood from the following description, the present invention offers a method and apparatus for rapidly analysing isoforms of proteins and other heteroforms, which has not been possible to achieve before.

Flow Matrix

The material of the flow matrix (including the separation zone and the detection zone) may be of the same type as that previously utilized in so-called immunochromatographic determination methods and defines the room in which sample components (including analytes) and reactants are transported, provided, of course, that the material permits flows in different directions. The inner surface of the matrix, i.e. the surface of the flow channels in the matrix, should be sufficiently hydrophilic to permit aqueous media, such as buffer, serum, plasma, blood, saliva etc, to be transported through the matrix. This transport may be achieved or assisted by capillary forces, either by capillary forces in the matrix itself or in an auxiliary means, such as an absorbent element (e.g. a sucking pad of cellulose or the like) brought in contact with matrix. The capillary flow may optionally be further assisted by pressure or suction applied by a pump device. The smallest inner dimension (for round channels measured as a diameter) should be sufficiently great to permit transport through the matrix of analyte and added reactants, Typically, suitable matrices may be selected among those having flow channels of a smallest inner dimension in the range of 0.01–1000 $\mu$m, with preference for 0.4–100 $\mu$m if the matrix has a system of communicating flow channels. Flow channels having their smallest dimension in the upper part of the broad range (up to 1000 $\mu$m) are primarily useful for flows driven by externally applied pressure/suction.

Presently, it is preferred that the flow matrix is in the form of a membrane, usually with a thickness less than about 500 $\mu$m, e.g. in the range of from about 25 $\mu$m to about 500 $\mu$m, and preferably less than about 150 $\mu$m, e.g. in the range of from about 75 to about 150 $\mu$m. Other types of matrices may, however, also be contemplated, such as a gel or a silicon (or glass) plate or chip with etched interconnected channels, etc. as is per se well known in the art.

Suitable matrices are often built up from a polymer, for example nitrocellulose, polyester, polyethersulphone, nylon, cellulose nitrate/acetate, cellulose, regenerated cellulose. Advantageously, membranes of such materials may be provided with a tight backside or backing of e.g. polyester.

The homogeneity of the flow matrix material affects its chromatographic quality and may therefore be reflected in terms of theoretical plate height. The lower height of the theoretical plate, the better the material. For example, a membrane for use in the present invention should preferably have a height of theoretical plate (HETP) of less than about 500 $\mu$m, especially less than about 100 $\mu$m.

Separation Zone

The separation zone and the detection zone may be integral parts of one and the same flow matrix or may be an assembly of separate parts. The separation zone, which optionally may comprise two or more subzones, may be based on various principles, permitting essentially aqueous systems to be used, including ion-exchange chromatography, chromatofocusing, gel filtration (size separation) (e.g. using a gel or a dense membrane), affinity (preferably a moderate binding constant of $<10^6$, especially $10^3$–$10^6$), including e.g. IMAC (immobilized metal chelate affinity chromatography), and hydrophobic interaction chromatography (HIC).

The separation zone exhibits a ligand/structure having a certain binding capability for the desired sample components (analytes and related heteroforms). The choice of ligand or structure, especially with regard to specificity, binding strength (affinity), and kinetics to suit the purposes of the present invention are readily apparent to a person skilled in the art. Ligands that make separation in the separation zone possible may thus be charged (anionic, cationic, amphoteric=ion-exchange ligands), amphoteric/amphiphilic, bioaffine, chelating, sulphur-containing (primarily thioether for so-called thiophilic affinity), or based on $\pi$-$\pi$ interaction, hydrophobic etc. Among biospecific affinity ligands, primarily so-called immunoligands are noted, i.e. antibodies and antigen-binding fragments thereof.

The ligands/structures in question may be structures physically introduced into the matrix in the manufacturing process, or may be anchored to the separation zone, either by covalent binding to the matrix, or via physical adsorption. The anchorage of the ligands/structures to the matrix may take place via a polymer or other substituent which in turn carries covalently, physically adsorptively, or biospecifically bound ligands that are used in the separation. Another possibility is deposition of polymer particles which exhibit a desired type of ligand. The particles may be of hydrophilic or hydrophobic character, and the ligand structure may be exhibited by a compound adsorbed or covalently bound to the particles. Regarding the technique for binding a separating ligand to the matrix, it may, for example, be referred to our previously filed International (PCT) applications WO 99/36780, WO 99/36776 and WO 99/36777 (the disclosures of which are incorporated by reference herein). In this connection it may be mentioned that there are commercially available membranes which have covalently bound ligands, for example DEAE cellulose paper (diethylaminoethyl) (DE81, Whatman International Ltd, England).

The ligand density (substitution degree) is selected to obtain the desired isocratic separation. Optionally, the separation zone may have different ligand densities or a gradient of ligand densities along the separation direction.

Examples of ion-exchange functional groups include anion exchangers, such as diethyl aminoethyl (DEAE), trimethyl hydroxypropyl (QA), quaternary aminoethyl (QAE), quaternary aminomethyl (Q), diethyl-(2-hydroxypropyl)-aminoethyl, triethyl aminomethyl (TEAE), triethylaminopropyl (TEAP), polyethyleneimine (PEI), and cation-exchangers, such as methacrylate, carboxymethyl (CM), orthophosphate (P), sulfonate (S), sulfoethyl (SE), sulfopropyl (SP).

After the ligand coating, the membrane is usually treated with a detergent or other suitable agent to substantially reduce or eliminate undesired background or unspecific adsorption effects of the membrane matrix as is per se known in the art.

The sample containing the analytes may be added directly on the flow matrix surface, but usually it is added to a separate sample application membrane or pad in liquid contact with the membrane, either in edge to edge contact therewith or, preferably, mounted on top of the flow matrix.

The conditions for the separation of the analytes in the separation zone is selected depending on the separation principle used, but generally the conditions are isocratic or with stepwise or continuously changed ion-strength. On the other hand, the transverse elution of the analytes from the separation zone is usually performed at isocratic conditions. Thus, in for example gel filtration, the separation buffer and elution buffer may be the same, whereas in ion-exchange chromatography it is normally necessary to use an elution buffer of high ionic strength for efficient elution of the separated analytes.

Detection Zone

In the detection zone, the analyte capture may be based on different principles such as biospecific capture, preferably immunochemical, or group-specific capture, e.g. binding of proteins based on the presence of hydrophobic groups. Presently, biospecific capture is preferred, a binding constant of $K>10^8$ then being desirable.

The capture reagent be bound to or immobilized in the detection part of the flow matrix as is well known in the art, e.g. in the same way as described above for the ligands in the separation zone.

As mentioned above, the detection zone preferably comprises a continuous line or band of capture reagent. In the case of a high concentration of one or more of the analytes, it may be necessary to use two, or occasionally even more detection lines or bands. Analogously, the ligand density in the detection zone may be varied depending on the mutual concentrations of the different analytes.

The detection zone should, of course, be sufficiently spaced from the separation zone for analyte not to spread to the detection zone before the separation is complete.

While it is desired that the release and transport of analyte from the separation zone to the detection zone be substantially complete, this is not necessary for the binding in the detection zone, provided that all the analytes bind to the same degree in the detection zone.

Depending on the type of flow matrix used, the elution flow from the separation zone may be guided to the detection zone through suitable delimiters, such as wax delimiters, laser made grooves etc.

The separation zone and the detection zone may be separate parts of different materials joined to form a combined flow matrix, but the two zones may, however, also be provided on an integral matrix, such as membrane or chip, by suitable chemical/physical modification thereof as is per se known in the art.

Detection Methods and Reagents

Detection and quantification of the analytes captured in the detection zone may take place in various ways. If the captured analytes are enzymatically active, they may be detected by their action on a suitable substrate, e.g. a colour change. Usually, however, a detectable reagent is added. Such a substrate or reagents may be added via a fluid flow in the matrix, either (i) from one of the sides transverse to the separation direction of the flow matrix (usually a long side), preferably in the opposite direction of the elution flow, or (ii) from one of the sides extending in the separation direction of the flow matrix (usually a short side), or (iii) on top of the matrix, usually near the detection zone via a pad or foldable part of the matrix such that the substrate or reagents may be transported by a fluid flow into the detection zone. In the last-mentioned case, a diffusive detection reagent may optionally be pre-deposited in the pad or foldable part. Such pre-deposition and folding structures are per se well known in the art. Excess of substrate or reagents will be removed by a buffer flow.

The detectable reagent is usually a biospecific affinity reactant which is labelled with an analytically detectable group, such as an enzymatically active group (e.g. colour formation upon action on substrate), fluorescent group, chromogenic group, hapten, biotin, radiolabel (autoradiography), particles, etc. A usual form of analytically labelled reactants is labelled antibody.

Labelled antibody may be used in (i) non-competitive techniques, such as sandwich technique, in which the capturer is an antibody which may be directed against the same antigen (=analyte) as the labelled antibody, or an antigen/hapten, or (ii) competitive techniques in which competition takes place between analyte and solid phase-bound analyte analogue for a limiting amount of anti-analyte antibody.

A particularly useful labelling group is particles, for example black-coloured carbon particles which may be measured directly, e.g. with a conventional type scanner. Optionally, the particles contain one of the above mentioned detectable groups, such as fluorophoric group or chromogenic group (fluorescent and coloured particles, respectively). Useful particles often have a size in the range 0.001 to 5 µm, with preference for the range 0.05 to 5 µm. The particles may be of colloidal dimensions, so-called sol (i.e. usually spherical and monodisperse having a size in the range 0.001 to 1 µm). Especially may be mentioned metal particles (for example, gold sol), non-metal particles (for example $SiO_2$, carbon, latex and killed erythrocytes and bacteria). Also particles of non-colloidal dimensions have been used. These have been more or less irregular and more or less polydisperse (for example, carbon particles <1 µm; see e.g. our WO 96/22532).

When particles are the label group, the complexes formed in the detection zone may often be detected visually or by optical measuring equipment (e.g. a CCD camera coupled to a computer with special software for image analysis or laser scanner).

For particles as label group, it may further be referred to e.g. WO 88/08534 (Unilever); U.S. Pat. No. 5,120,643 (Abbott Labs.); EP-A-284,232 (Becton Dickinson).

The invention is primarily intended for biological samples, for example, blood (serum, plasma, whole blood), saliva, tear fluid, urine, cerebrospinal fluid, sweat, etc. The invention is also applicable to other samples, such as fermentation solutions, reaction mixtures, etc.

ILLUSTRATIVE EMBODIMENT

In order to facilitate the understanding of the present invention, an embodiment thereof will now be described in more detail, by way of example only, with reference to FIGS. 1 and 2A to 2C of the drawings.

FIG. 1 illustrates schematically a membrane that may be used for the analysis of e.g. isoforms of proteins or other heteroforms in accordance with the method of the invention. The membrane consists in the illustrated case of two combined parts of different materials, a separation part 1 and a detection part 2, joined by a piece of adhesive tape (not shown) on the backside of the combined membrane and in liquid receiving contact with each other by a thin membrane band 3 as an overlap. This membrane band 3 is secured to the separation/detection membrane by a piece of adhesive tape 4. The separation part defines a separation zone on the combined membrane. The detection part 2 has a detection zone in the form of a line 5 of immobilized capture reagent for analytes, e.g. having a width of about 1 mm. Reference numeral 6 indicates an optional additional detection line to increase the measurement range. The short-sides of the membrane are indicated in FIG. 1 by a and c and the long-sides by b and d, respectively.

Figure 2A:
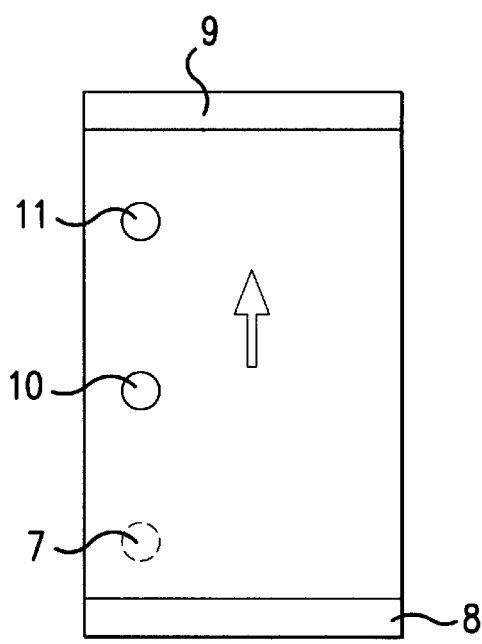
FIGS. 2A, 2B and 2C are schematic planar views of the apparatus in FIG. 1, each illustrating a different stage in the method of the present invention.

The membrane may be used as follows with reference to FIGS. 2A to 2C. After wetting the membrane, a sample containing two analytes to be analysed (referred to as analytes 1 and 2 below) is applied at 7 on the separation zone 1 (FIG. 2A). A pad 8 containing separation buffer is applied at short-side a of the membrane and a sucking pad 9 at the opposite short-side c. This will cause a buffer flow in the direction of the arrow in FIG. 2A, separating the two analytes as indicted by the dots at 10 (analyte 1) and 11 (analyte 2) in FIG. 2A.

Figure 2B:
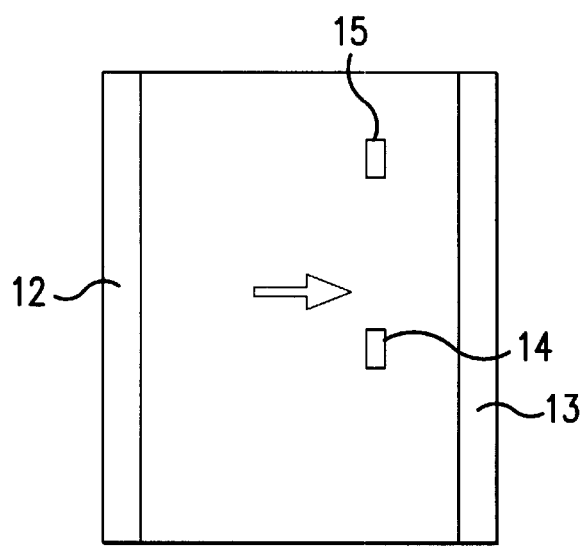

With reference to FIG. 2B, pads 8 and 9 are then removed and an eluent-containing pad 12 is mounted to the long-side d, and a sucking pad 13 is mounted to long-side b. This causes a flow of eluent in the direction of the arrow in FIG. 2B, transporting the separated analytes 1 and 2 to the detection zone where they are captured by the immobilized reagent line at positions 14 and 15, respectively, along the line.

Figure 2C:
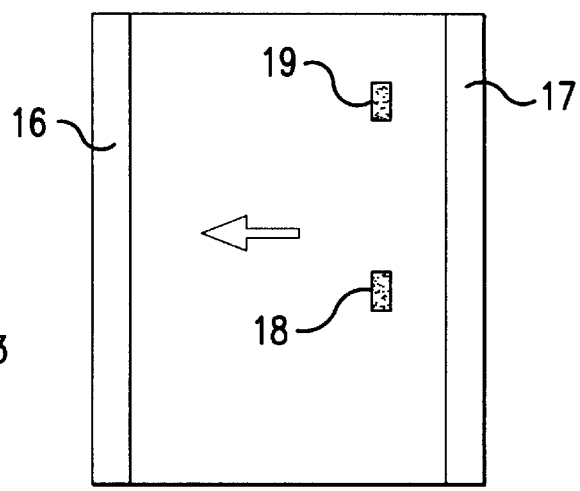

Then, with reference to FIG. 2C, the pads 12 and 13 are removed and replaced by a sucking pad 16 at the long-side d, and a container 17 with a solution or suspension of labelled reactant at the long-side b. Thereby, labelled reactant will migrate in the direction of the arrow and bind to the captured analytes 1 and 2 at 18 and 19 in FIG. 2C. The labelled complexes, and thereby the corresponding analytes 1 and 2, may then be detected and quantified by reading the intensity of the signals from the label along the detection line and calculating the respective amounts. In case the label is carbon particles, the measurements may advantageously be performed with a scanner.

The above described manual initiation and stopping of the flows are, of course, only given for purpose of illustration, and more sophisticated means therefor are readily apparent to a person skilled in the art, such as, for example, so-called imprinted liquid circuits (see e.g. WO 93/10457) etc.

A specific example where the method of the present invention is used for the analysis of isoforms of transferrins is described below.

EXAMPLE 1

Determination of Isoforms of Transferrin (i) Preparation of Separation Membrane with Anion-exchanging Properties A sheet of nitrocellulose membrane (3 µm, nitrocellulose on polyester backing, Whatman International Ltd, England) was placed in a solution of 0.03% polyethyleneimine (PEI, Sigma, St Louise, Mo., USA). The mixture was shaken for three hours and the membrane was then placed in 0.1% Tween 20 for 30 minutes, dried in air and then stored in a plastic bag at +4° C.

(ii) Preparation of Detection Membrane

Anti-transferrin monoclonal antibody, 3 mg/ml, was sprayed onto strips (29 cm×4 cm) of nitrocellulose membranes (5 µm, on polyester backing, Whatman International Ltd, England) in two 1 mm broad lines in the centre of the strip, separated by 2 mm and in parallel with the long side of the strip. The spraying equipment (IVEK Linear Striper IVEK Corporation, Vermont, USA) delivered 1 µl/cm. The membranes were dried at room temperature and stored in a plastic bag at +4° C.

(iii) Preparation of Combination Membrane

The separation membrane was cut to 1.5×5 cm and the detection membrane was cut to 2×5 cm such that the two antibody lines were located centrally on the membrane and in parallel with the long side. The two membranes were put tightly together along the long sides and joined by means of adhesive tape on the underside. A piece of nitrocellulose membrane (0.2 cm×5 cm, 8 µm, A99, Schleicher and Shuell, Dassel, Germany) was placed on the top side of the two membranes as an overlap. This membrane was anchored by means of a 1×4 cm self-adhesive polyester film (Gelman adhesive polyester film, 3 mil) placed such that 0.5 cm at the short side end on the formed combined separation/detection membrane remained uncovered. Below, the two short sides of the combination membrane are referred to as a and c, respectively, and the two long sides as b and d, respectively (see FIG. 1).

(iv) Carbon Particle Conjugate

Carbon Particle Suspension (Stock Solution)

3 g of carbon particles (sp 4, Degussa, Germany) were suspended in 250 ml of 5 mM borate buffer, pH 8.4, and sonicated (VibraCell 600 W, 1.5 cm probe) in an ice-bath for 4×5 minutes at 100% amplitude and 5+5 seconds pulse.

Carbon Particle Conjugate

75 µg/ml of anti-transferrin monoclonal antibody and carbon suspension (250 µg/ml) were mixed for 3 hours. Bovine serum albumin (BSA), corresponding to 1% final concentration, were added and the particles were mixed for additionally 30 minutes and then washed by means of centrifugation and decanting in 0.1 M borate buffer, pH 8.5 (containing 1% BSA and 0.05% $NaN_3$) and diluted to 3.7 mg carbon/ml with wash buffer. The ready carbon particle conjugate was stored at +4° C. in wash buffer.

(v) Sample Materials

Tetrasialo Transferrin, Trisialo Transferrin and Disialo Transferrin

These iso-transferrins were isolated from an iron-saturated preparation of transferrin (Sigma, St Louis, Mo., USA) by ion-exchange chromatography on Mono Q (Amersham Pharmacia Biotech AB, Uppsala, Sweden).

Asialo Transferrin

An iron-saturated preparation of transferrin (Sigma, St Louis, Mo., USA) was treated with neuraminidase (Behring ORKD, Germany), and asialo transferrin was then isolated by ion-exchange chromatography on Mono Q (Amersham Pharmacia Biotech AB, Sweden).

The various isoforms were diluted in 0.2% BSA, 0.1% bovine gammaglobulin, 0.1% Tween 20, 0.1 mM $Fe^{3+}$-citrate, 1 mM $NaHCO_3$ and 0.05% $NaN_3$ to the concentrations 2–6.5 µg transferrin/ml.

Isoelectric Points (pI)

The pI's were determined for the respective isoform preparation by repeated isoelectric focusing in Phast System (Amersham Pharmacia Biotech AB, Uppsala, Sweden). Asialo transferrin pI=5.66; disialo transferrin pI=5.56; trisialo transferrin pI=5.46; tetrasialo transferrin pI=5.32 and pentasialo transferrin pI=5.21. Amersham Pharmacia Calibration Kit, 17-0472-01, 2.5–6.5 was used for calibration.

Transferrin Standard

Asialo transferrin prepared as described above was diluted in 20 mM Bis-Tris, pH 6.37, containing 0.2% BSA, 0.1% Tween 20, 0.1 mM $Fe^{3+}$ citrate, 1 mM $NaHCO_3$ and 0.05% $NaN_3$ to the concentrations 0.07–16.6 µg transferrin/ml and was used as a standard.

(vi) Standard Protocol for Combined Separation and Immunochemical Determination

Step 1. Wetting of Membrane from Short Side a to Short Side c

The combination membrane is wetted by adding elution buffer to a 1×3.5×0.5 cm PVA sponge (PVA D, 60 µm, Kanebo Ltd, Japan) and then placing the sponge along short side a of the pad. To the opposed short side c of the membrane is mounted a 2×3.5 cm sucking cellulose pad (GB 004, Schlecher and Schuell). When the elution buffer front has reached the cellulose pad, the PVA sponge is removed. For analysis (a) below, the elution buffer was 20 mM Bis-Tris, 0.1% Tween 20, 5 mM NaCl, pH 6.12; and for analysis (b) below, the elution buffer was 20 mM Bis-Tris, 0.1% Tween 20, 15 mM NaCl, pH 6.32.

Step 2. Sample Application and Elution from Short Side a to Short Side c 0.5 µl of sample (2–6.5 µg/ml) is placed on the middle of the separation membrane, 0.5 cm from the short side a. The PVA sponge with elution buffer is added and the elution is continued for 4 minutes. Then the PVA sponge and the sucking pad are removed.

Step 3. Elution from Long side d (Separation Membrane) to Long Side b (Detection Membrane)

Along long side b (detection membrane) is mounted a 2×5 cm cellulose pad (GB 004, Schlecher and Schuell), and along long side d is placed a 1×5×0.5 cm PVA sponge (PVA D, 60 µm, Kanebo Ltd, Japan) wetted by elution buffer (20 mM Bis-Tris, 200 mM NaCl, 0.1% Tween 20, pH 6.29). The elution is continued for 4 minutes and the flow is stopped by removing the PVA sponge and the sucking pad.

Step 4. Reaction with Carbon-anti-transferrin

A 2×5 cm sucking cellulose pad (GB 004, Schlecher and Schuell) is mounted along long side d (separation membrane part), and then long side b is placed in a container with carbon-anti-transferrin, 0.25 mg carbon/ml in 40% trehalose, 1% Tween 20, 1% bovine albumin, 0.1 M borate buffer, pH 8.5, 0.05% $NaN_3$. The carbon particle conjugate is allowed to pass the detection lines for 2 minutes, and the combination membrane is then removed from the container, the sucking pad is removed and the combination membrane is left to dry.

Step 5. Detection of Blackening and Calculation of Transferrin Concentration

The membrane is placed in a scanner (Agfa Acus II Scanner) for mesurement of a grey scale along the detection lines. The grey scale is read with a 12 bits grey scale resolution (4096 levels) and 600 points per inch (ppi) optical resolution. The image obtained is digitalised and the intensity values are processed by means of Microsoft Excel. The average value of the intensity along the short side of the detection line (1 mm=23 grey scale values) are calculated and the chromatogram for 4 cm along the detection line may be illustrated graphically.

For calculating the concentration of transferrin, a dilution series of asialo transferrin is used where 0.5 µl of sample has been dispensed onto the separation membrane and then directly eluted off (steps 3–5). The top intensity of the respective standard point is measured, a standard curve is constructed by means of a curve-fitting program (GraphPad Prism® nonlinear fit) and the transferrin concentration for the chromatograms may be calculated.

Figure 3:
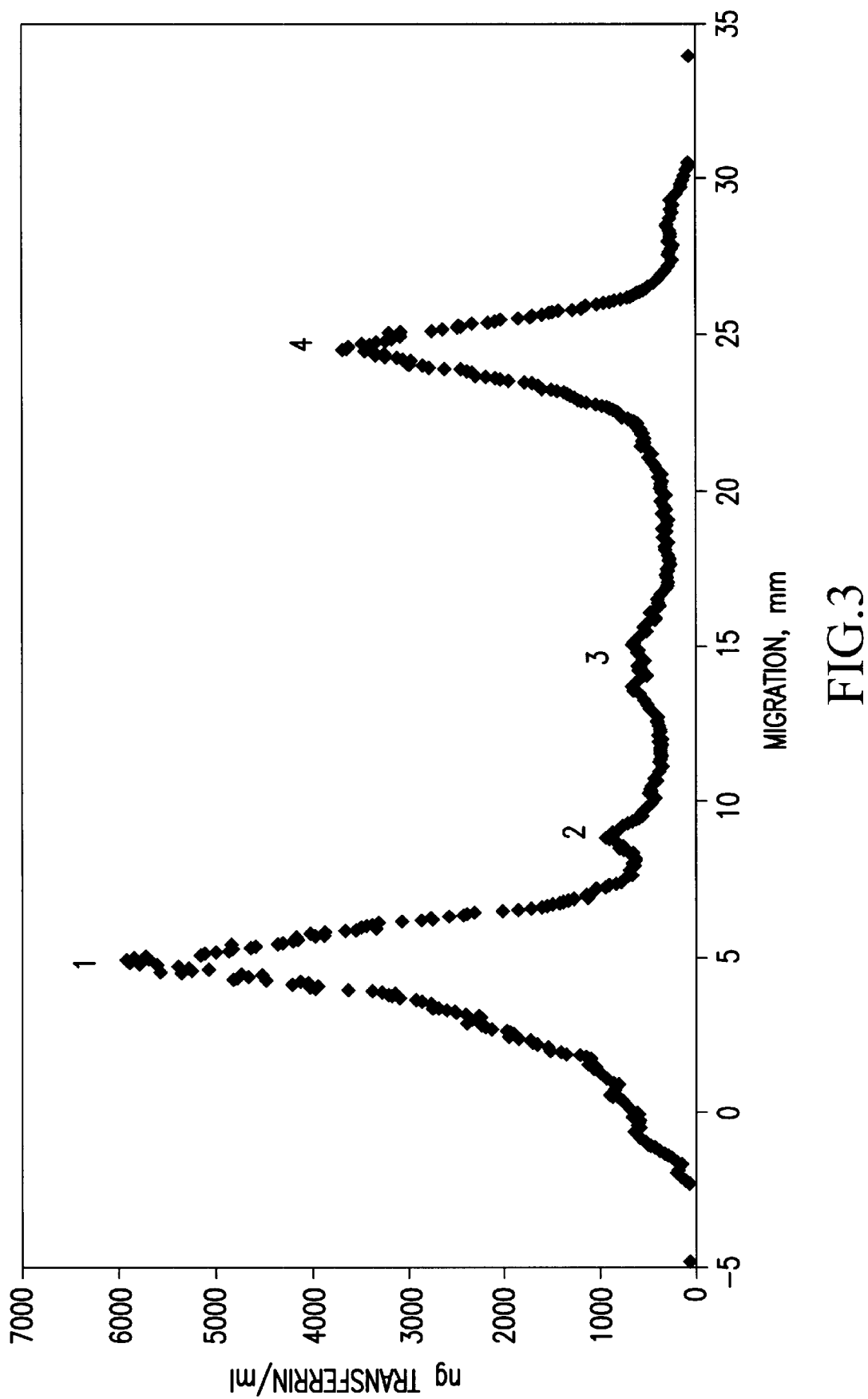
FIG. 3 is a diagram showing the detected intensity curves for transferrin isoforms analyzed by the method of the present invention.
Figure 4:
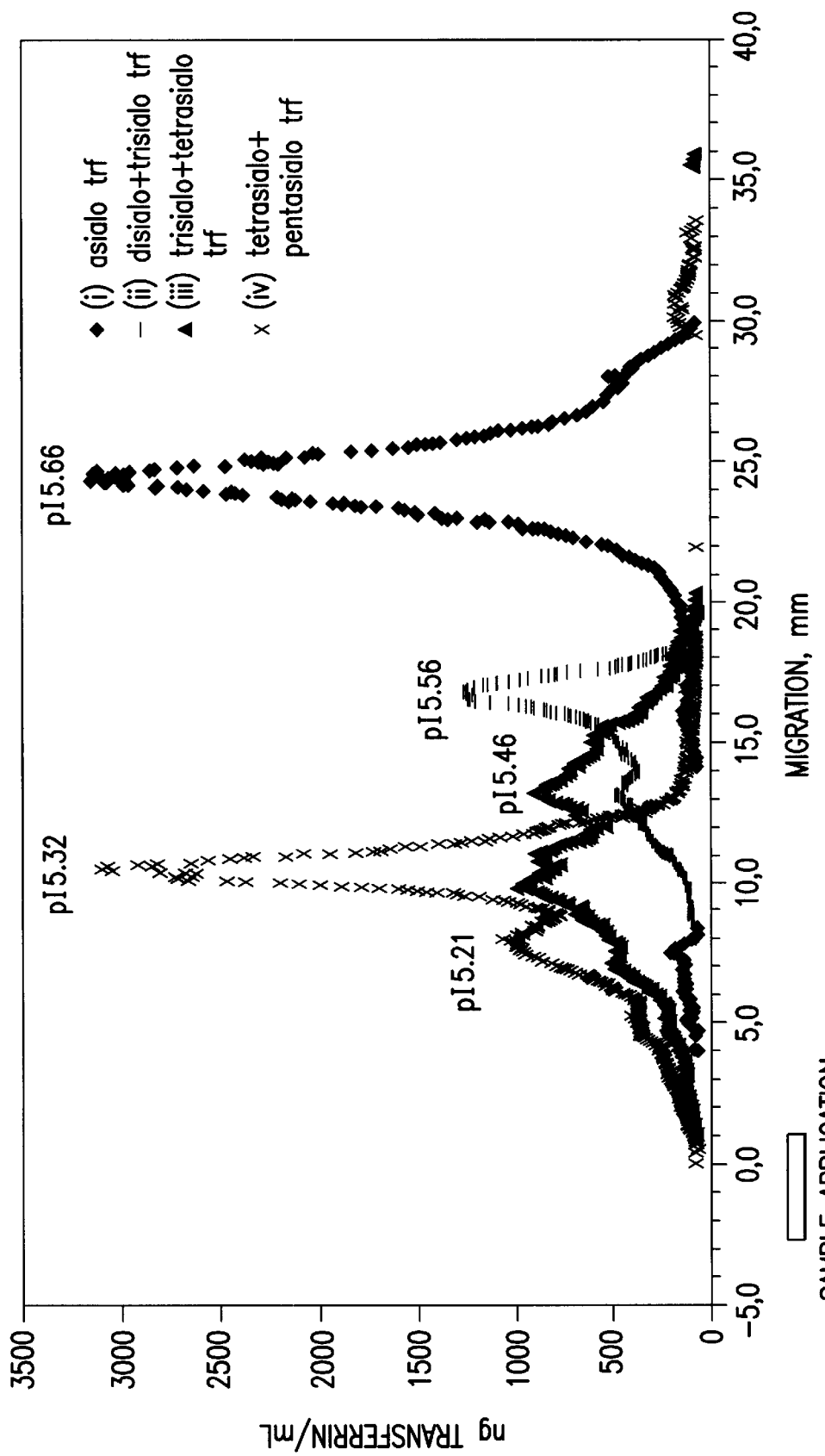
FIG. 4 is a diagram showing four superposed intensity curves for detected transferrin isoforms from separate analyses by the method of the present invention.

(vi) Analyses a) A prepared sample containing asialo transferrin, disialo transferrin, trisialo transferrin and tetrasialo transferrin was analysed according to the standard protocol above, and the signal intensity curves obtained are shown in FIG. 3. In the diagram, numeral 1 indicates the peak for tetrasialo transferrin, 2 is trisialo transferrin, 3 is diasialo transferrin, and 4 is asialo transferrin.

b) prepared samples containing (i) asialo transferrin, (ii) disialo+trisialo transferrin, (iii) trisialo+and tetrasialo transferrin, and (iv) tetrasialo+pentasialo transferrin, respectively, were analysed according to the standard protocol above, and the results are shown in FIG. 4. The different peaks are identified in the top right hand corner of the diagram. Also the isoelectric point values of the peaks are indicated.

As demonstrated by FIGS. 3 and 4, the method of the invention permits excellent separation and quantification of isoforms in a sample. For example, a resolution of 0.1 pI unit is readily achieved as shown in FIG. 4.

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

What is claimed is:

1. A method for qualitative, semi-quantitative or quantitative determination of at least two analytes in an aqueous sample containing or suspected of containing the analytes, said method comprising the steps of:

(i) providing a flow matrix comprising a separation zone extending in a first dimension thereof, and a detection zone extending in said first dimension adjacent the separation zone, said detection zone comprising an immobilized reagent capable of capturing said analytes through biospecific interaction therewith, (ii) applying said sample to the flow matrix at or upstream of the separation zone, (iii) initiating a first essentially aqueous fluid flow in the flow matrix along the separation zone in said first dimension to transport the analytes through the separation zone to be separated therein, (iv) interrupting said first fluid flow and initiating a second essentially aqueous fluid flow in a second dimension of the flow matrix substantially transverse to said first dimension towards the detection zone to transport said separated analytes to the detection zone to be captured therein by said immobilized reagent, and (v) determining the analytes in the detection zone, wherein the fluid flows in said matrix are assisted by capillary forces, and wherein the fluid transport in the flow matrix is at least assisted by an absorbent element which may be separate from or integral with the flow matrix.

2. The method according to claim 1, wherein the flow matrix is at least substantially planar.

3. The method according to claim 1 or 2, wherein the separation zone and the detection zone are arranged in the same plane and said first and second fluid flows are lateral flows.

4. The method according to claim 1 or 2, wherein the separation zone and the detection zone are arranged on top of each other and said first fluid flow is lateral and said second fluid flow is in depth in the flow matrix.

5. The method according to claim 1, wherein the fluid transport in the flow matrix at least partially is effected by capillary forces in the matrix itself.

6. The method according to claim 1, wherein the flow matrix is wetted by an essentially aqueous fluid prior to starting the assay.

7. The method according to claim 1, wherein the determination of analytes (v) comprises reacting said captured analytes with a detectable reagent.

8. The method according to claim 7, wherein the detectable reagent is an immunochemical reagent.

9. The method according to claim 1, wherein the determination of analytes (v) comprises reacting unreacted immobilized reagent in the matrix with detectable analyte or a detectable analyte analogue.

10. The method according to claim 7, 8 or 9, wherein said detectable reagent, analyte or analyte analogue comprise a detectable label.

11. The method according to any one of claims 7 to 9, wherein said detectable reagent, analyte or analyte analogue is introduced by a third fluid flow.

12. The method according to claim 11, wherein said third fluid flow is a lateral flow applied from one side of said flow matrix.

13. The method according to claim 1, wherein the separation in said separation zone is based on chromatography.

14. The method according to claim 13, wherein said chromatography is selected from the group consisting of ion-exchange chromatography, chromatofocusing, size exclusion chromatography, affinity chromatography, and hydrophobic interaction chromatography.

15. The method according to claim 1, wherein said separation zone comprises a gradient in said first direction with regard to separating capability.

16. The method according to claim 1, wherein said analytes are heteroforms of a biomolecule.

17. The method according to claim 16, wherein said heteroforms have different charges.

18. The method according to claim 16 or 17, wherein said analytes are glycoproteins.

19. The method according to claim 1, wherein said flow matrix comprises a membrane.

20. The method according to claim 1, wherein said matrix comprises a membrane having particles deposited therein.

21. The method according to claim 1, wherein said detection zone comprises at least two parallel detection lines or bands containing immobilized reagent.

22. The method according to claim 1, wherein the binding of the analyte in the detection zone is by an immunochemical interaction.

23. An apparatus for determining analytes in a sample, which apparatus comprises:
   (i) a flow matrix having a separation zone and a detection zone extending in a spaced parallel relationship in a first dimension of the flow matrix, wherein the detection zone comprises immobilized reagent capable of binding the analytes through biospecific interaction therewith,
   (ii) means for initiating a first essentially aqueous fluid flow in the flow matrix along the separation zone in said first dimension of the flow matrix,
   (iii) means for initiating a second essentially aqueous fluid flow in a second dimension of said flow matrix substantially transverse to the said first dimension towards the detection zone,
   such that when a sample containing the analytes is introduced into to the separation zone, the analytes may be separated in the separation zone by said first fluid flow through the separation zone and transported by said second fluid flow to the detection zone where the analytes are bound to the immobilized reagent to be determined.

24. The apparatus according to claim 23, wherein the flow matrix permits capillary force assisted fluid flow therethrough.

25. The apparatus according to claim 23 or 24, wherein the flow matrix is at least substantially planar.

26. The apparatus according to claim 23 or 24, wherein the separation zone and the detection zone are arranged in the same plane and said first and second fluid flows are lateral flows.

27. The apparatus according to claim 23 or 24, wherein the separation zone and the detection zone are arranged on top of each other and said first fluid flow is lateral and said second fluid flow is in depth in the flow matrix.

28. The apparatus according to claim 23, wherein the separation zone is based on choromatography selected from the group consisting of ion-exchange chromatography, chromatofocusing, size exclusion chromatography, affinity chromatography, and hydrophobic interaction chromatography or comprises a gradient in said first direction with regard to separating capability.

29. The apparatus according to claim 23, wherein the flow matrix comprises a membrane or a membrane having particles deposited therein.

30. The apparatus according to claim 23, wherein the detection zone comprises at least two parallel detection lines or bands containing immobilized reagent.

31. The apparatus according to claim 23, which apparatus comprises means for creating liquid suction in the flow matrix.

32. The apparatus according claim 31, wherein said means for creating liquid suction comprise an absorbent member at the downstream end of the flow matrix.

33. The apparatus according to claim 23, which apparatus comprises means for supplying flow liquid to the flow matrix.

* * * * *